(12) United States Patent
Matsuo et al.

(10) Patent No.: US 9,839,588 B2
(45) Date of Patent: Dec. 12, 2017

(54) SKIN EXTERNAL PREPARATION COMPRISING AN AQUEOUS DISPERSION OF FINELY DISPERSED WAX, NONIONIC SURFACTANT, AND IONIC WATER-SOLUBLE THICKENER

(75) Inventors: Akira Matsuo, Yokohama (JP); Eriko Takeoka, Yokohama (JP); Eiko Sato, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 71 days.

(21) Appl. No.: 13/260,379

(22) PCT Filed: Mar. 30, 2010

(86) PCT No.: PCT/JP2010/055658
§ 371 (c)(1),
(2), (4) Date: Apr. 16, 2012

(87) PCT Pub. No.: WO2010/113930
PCT Pub. Date: Oct. 7, 2010

(65) Prior Publication Data
US 2012/0189675 A1 Jul. 26, 2012

(30) Foreign Application Priority Data

Mar. 31, 2009 (JP) ................................. 2009-087818
Mar. 31, 2009 (JP) ................................. 2009-087819

(51) Int. Cl.
| | |
|---|---|
| *A61K 8/92* | (2006.01) |
| *A61K 8/31* | (2006.01) |
| *A61K 8/34* | (2006.01) |
| *A61K 8/39* | (2006.01) |
| *A61K 8/70* | (2006.01) |
| *A61K 8/81* | (2006.01) |
| *A61K 8/86* | (2006.01) |
| *A61K 8/891* | (2006.01) |
| *A61Q 19/00* | (2006.01) |
| *A61K 8/04* | (2006.01) |
| *A61Q 19/08* | (2006.01) |

(52) U.S. Cl.
CPC .............. *A61K 8/044* (2013.01); *A61K 8/925* (2013.01); *A61K 8/927* (2013.01); *A61Q 19/08* (2013.01); *A61K 2800/592* (2013.01)

(58) Field of Classification Search
CPC .......................... Y10S 514/941; Y10S 514/943
See application file for complete search history.

(56) References Cited

U.S. PATENT DOCUMENTS

| | | | | |
|---|---|---|---|---|
| 5,306,488 | A * | 4/1994 | Vanlerberghe et al. | 424/70.8 |
| 6,156,804 | A | 12/2000 | Chevalier et al. | |
| 7,785,613 | B2 | 8/2010 | Collin et al. | |
| 2002/0022009 | A1* | 2/2002 | De La Poterie | A61K 8/044 424/63 |
| 2004/0052744 | A1* | 3/2004 | Maillefer et al. | 424/70.1 |
| 2010/0316581 | A1* | 12/2010 | Takeoka et al. | 424/59 |

FOREIGN PATENT DOCUMENTS

| | | | |
|---|---|---|---|
| DE | WO 0243673 A2 * | 6/2002 | ............ A61K 8/342 |
| JP | 10-259114 | 9/1998 | |
| JP | 2001-163721 | 6/2001 | |
| JP | 2002-179536 | 6/2002 | |
| JP | 2008-24630 | 2/2008 | |
| WO | WO 2009072629 A1 * | 6/2009 | |

OTHER PUBLICATIONS

Google Patent Machine Translation, Dolhaine et al. WO2002043673, accessed Mar. 1, 2016.*
Google Patent Machine Translation)), as evidenced by "lauryl glycoside", accessed at http://www.thegoodcentscompany.com/data/ rw1307131.html on Mar. 1, 2016.*
Google Patent Machine Translation)), as evidenced by BASF, Plantacare 1200 UP, accessed at https://e-applications.basf-ag.de/data/basf-pcan/pds2/pds2-web.nsf/C7E518BAACA7856EC12576570041964F/$File/Plantacare_r_1200_UP_E.pdf on Mar. 1, 2016.*
Espacenet Bibliographic Data for Japanese Publication No. 2002179536 published Jun. 26, 2002, one page.
Espacenet Bibliographic Data for Japanese Publication No. 2001163721 published Jun. 19, 2001, one page.
Espacenet Bibliographic Data for Japanese Publication No. 2008024630 published Feb. 7, 2008, one page.
Espacenet Bibliographic Data for Japanese Publication No. 10259114 published Sep. 29, 1998, one page.

* cited by examiner

*Primary Examiner* — Kortney L. Klinkel
*Assistant Examiner* — Lisbeth C Robinson
(74) *Attorney, Agent, or Firm* — Rankin, Hill & Clark LLP

(57) ABSTRACT

A skin external preparation includes a finely dispersed wax composition that is solid or semisolid at room temperature, a nonionic surfactant, an aqueous dispersion medium, and an ionic water-soluble thickener, and optionally further contains at least one of silicone oil and fluorinated oil which is liquid at room temperature, and the mass ratio of the nonionic surfactant to the wax being 1.0 or more, the particle size of the finely dispersed wax is 500 nm or less, and it substantially contains no ionic surfactants therein.

10 Claims, No Drawings

SKIN EXTERNAL PREPARATION COMPRISING AN AQUEOUS DISPERSION OF FINELY DISPERSED WAX, NONIONIC SURFACTANT, AND IONIC WATER-SOLUBLE THICKENER

TECHNICAL FIELD

The present invention relates to skin external preparations that comprise a finely dispersed wax composition (=wax microdispersion composition) in which wax is finely dispersed in a solid or semisolid state in an aqueous dispersion medium. More particularly, the invention relates to skin external preparations which are stable and are superior in a skin-tension feeling effect or skin-elasticity feeling effect after application therewith to the skin. The present invention also relates to skin external preparations which are excellent in adhesiveness to the skin and have a non-sticky feeling, in addition to the above described stability and the skin-tension feeling effect.

BACKGROUND ART

In anti-aging cosmetics or the like, a skin-tension feeling after application is important as a feeling by which a cosmetic benefit can be promptly realized. Heretofore, there has been much to use a water-soluble polymer such as polyvinyl alcohol to produce a skin-tension feeling, but its effect has not always been satisfied, and therefore, a further improvement for the skin-tension feeling has been required. Furthermore, it is more desirable to provide cosmetics which are excellent in adhesiveness to the skin and have a non-sticky feeling, in addition to the skin-tension feeling effect.

The prior art documents which disclose the arts related to the present invention are as follow.

That is, as shown in Patent Documents 1-3, in order to solve disadvantages of cosmetics such as stickiness and dazzling that result from the incorporation of wax in cosmetics, the applicant of the present invention has proposed a technology in which wax in finely dispersed in a solvent to make a wax emulsion, thereby producing a finely dispersed wax composition that is not only free from the above-mentioned defects but also characterized by high degrees of stability and safety. However, each of the finely dispersed was compositions described in Patent Documents 1-3 is intended to utilize the performance such as lusting and shape-retaining properties of wax itself so that they can be applied to hair cosmetics such as setting lotions and heir mousses and lustering preparations, and none of these patent documents describe or suggest the idea of the present invention, i.e., obtaining the skin-tense feeling after application. In addition, none of these patent documents describe or suggest for obtaining the non-sticky feeling after application and the skin-adhesiveness feeling.

Patent Documents 4-5 also describe hair cosmetic compositions comprising microdispersions of wax; however, the technology disclosed in each of these references is also intended to utilize the performance such as lustering and shape-retaining properties of wax itself so that they can be applied to hair cosmetics such as setting lotions and hair mousses and lustering preparations, and none of these patent documents describe or suggest the idea of the present invention, i.e., obtaining the skin-tense feeling after application. In addition, none of these patent documents describe or suggest for obtaining the non-sticky feeling after application and the skin-adhesiveness feeling.

Patent Document 6 describes the invention related to a wax dispersion whose mean particle size ranges from 0.5 to 100 μm, which comprises a wax phase containing a specified oil component or wax component, and a water phase. However, the particles having such large size are worried about the stability of the dispersion during a long-term storage. In addition, the wax dispersion described in the patent document is used for coating on a base material such as tissue paper for use in production of wet wipe and dry wipe, and there is neither description nor suggestion for incorporating a wax dispersion into an external skin preparation thereby to improve a skin-tense feeling after application. It also does not describe nor suggest with respect to the non-sticky feeling after application and the skin-adhesiveness feeling. Patent Document 6 does not describe regarding the mass ratio of nonionic surfactant to wax; each the ratio of the nonionic surfactant to wax in the wax dispersions shown in Examples (Table 1; [0081]) is less than 1.0.

Patent Document 7 describes the invention related to a pearlescent wax which comprises 30-60 mass % of wax consisting of amorphous and crystalline components, 5-20 mass % of nonionic surfactant and/or amphoteric surfactant, and water if required. That is, the mass ratio of nonionic surfactant to wax in the invention of Patent Document 7 is less than 1.0. Further, Patent Document 7 does not describe nor suggest the step for obtaining a solubilized state of wax under heating in the range of the solubilizing temperature over the melting point of the wax in production of the pearlescent wax, and there is also neither description nor suggestion on dispersion of extremely fine wax particles of 500 nm or less in size. The obtained finely crystallized wax particles in Examples in Patent Document 7 are as large as 12 μm, 13 μm in size (Table 1 in [0077]), and according to the section of Background Art in the patent document, the pearlescent wax is described to have to have particle sizes of generally 5-60 μm ([0002]).

Patent Document 8 describes the invention related to a self-emulsifying base containing an anhydrous wax mixture and an anionic or nonionic emulsifier with an HLB value of at least 10 (claim 8), as well as the use of the above-mentioned anhydrous wax mixture or self-emulsifying base in order to increase the viscosity of an emulsion, particularly oil-in-water type emulsion (claims 13 and 14). In Patent document 8, however, there is neither description nor suggestion on the step for obtaining a solubilized state of wax under heating in the range of the solubilizing temperature over the melting point of the wax in production of the above-mentioned base, and there is also neither description nor suggestion on dispersion of extremely fine wax particles of 500 nm or less in size. In Examples in Patent Document 8, the use of a nonionic surfactant as an emulsifier is described only in the experimental examples shown in Tables 5-7, wherein the mass ratio of "the nonionic surfactant relative to the wax" is less than 1.0 in every experimental example ([0057]-[0059]).

In this connection, it is known that a fluid oil or solid or semisolid wax is compounded as an oil component in an O/W emulsified composition (cream, emulsion, etc.); in such a case, when the compounded ratio of solid or semisolid wax is high, then the stability of the emulsified product becomes worse, and when the ratio of the fluid oil is high, then a skin-tension feeling owing to the solid or semisolid wax becomes difficult to perceive; thus, it is difficult to manage both of stability and feeling in use (skin-tension feeling, non-sticky feeling, etc.).

PRIOR ART REFERENCES

Patent Documents

Patent Document 1: JP 10-324617A
Patent Document 2: JP 11-286418A
Patent Document 3: JP 11-263915A
Patent Document 4: JP 4-230616A
Patent Document 5: JP 3-2112A
Patent Document 6: JP 2006-516029A
Patent Document 7: JP 2004-523519A
Patent Document 8: JP 2007-531777A

SUMMARY OF THE INVENTION

Problems that the Invention is to Solve

The present invention has been accomplished in light of the above-mentioned problems of the prior art: One object is to provide skin external preparations which are stable and are superior in a skin-tension feeling effect or skin-elasticity feeling effect after application therewith to the skin. Additionally, another object of the invention is to provide skin external preparations which are excellent in adhesiveness to the skin and have a non-sticky feeling, in addition to the above described stability and the skin-tension feeling effect.

Means for Solving the Problems

In order to solve the aforementioned problems, the present inventors made intensive studies and found that, in the production of a finely dispersed composition where wax being solid or semisolid at ordinary temperature (in particular, natural wax, such as carnauba wax and candelilla wax, etc.) is finely dispersed in an aqueous dispersing medium, by incorporating a certain thickener and so on into the composition, as well as restricting the compound ratio of the wax to a nonionic surfactant in the specified range, and furthermore preferably conducting the production under a specified heating condition, then the resulting wax microdispersion composition is stable and superior in feeling in use; the present invention has been accomplished on the basis of this finding.

The present invention provides a skin external preparation comprising a finely dispersed wax composition in which the wax is finely dispersed in a solid or semisolid form in an aqueous dispersion medium, which preparation is characterized in that the above finely dispersed wax composition contains a wax being solid or semisolid at ordinary temperature, a nonionic surfactant, an aqueous dispersion medium, and an ionic water-soluble thickener, the mass ratio of the nonionic surfactant to the wax being 1.0 or more, the particle size of the finely dispersed wax is 500 nm or less, and it substantially contains no ionic surfactants therein.

The present invention also provides a skin external preparation as described above, wherein the finely dispersed wax composition further contains silicone oil and/or fluorinated oil which is liquid at ordinary temperature.

Advantage of the Invention

According to the present invention, there are provided skin external preparations which are stable and are superior in a skin-tension feeling effect or skin-elasticity feeling effect after application therewith to the skin. Additionally, there are provided skin external preparations which are excellent in adhesiveness to the skin and have a non-sticky feeling, in addition to the above described stability and the skin-tension feeling effect.

MODE FOR CARRYING OUT THE INVENTION

Hereinafter, the present invention is described in detail.
In the following description, "POE" means polyoxyethylene and "POP" means polyoxypropylene.

[Finely Dispersed Wax Composition]

One embodiment of the finely dispersed wax composition which is used in the skin external preparations of the present invention contains a wax that is solid or semisolid at ordinary temperature, a nonionic surfactant, an aqueous dispersion medium, and a water-soluble thickener, and the wax being finely dispersed in solid or semisolid form in the aqueous dispersion medium.

The other embodiment of the finely dispersed wax composition which is used in the skin external preparations of the present invention contains a wax that is solid or semisolid at ordinary temperatures, a nonionic surfactant, an aqueous dispersion medium, a water-soluble thickener, and silicone oil and/or fluorinated oil which is liquid at ordinary temperature, and the wax being finely dispersed in solid or semisolid form in the aqueous dispersion medium.

<Wax>

The wax which is used in the present invention assumes a solid or semisolid state at ordinary temperatures and specific examples include, but are not limited to, beeswax, candelilla wax, cotton wax, carnauba wax, bayberry wax, insect wax (wax secreted by *Ericerus pela*), spermaceti, montan wax, bran wax (=rice wax), capok wax, Japan wax, lanolin acetate, liquid lanolin, sugar cane wax, esters of lanolin fatty acids and isopropyl alcohol, hexyl laurate, reduced lanolin, jojoba wax, hard lanolin, shellac wax, beeswax, microcrystalline wax, paraffin wax, POE lanolin alcohol ethers, POE lanolin alcohol acetates, POE cholesterol ethers, esters of lanolin fatty acids and polyethylene glycol, fatty acid glycerides, hydrogenated castor oil, petrolatum, and POE hydrogenated lanolin alcohol ethers. Among them, natural waxes, such as carnauba wax and candellia wax, etc., and the ones having a rather high melting point (80° C. or above) are preferably used in view of a long-time storage stability.

It should be noted that the above-listed waxes may be used in admixture and even if they are mixed with other solid or liquid oil components, the mixtures can be used within the range where they are in solid or semisolid form at ordinary temperatures.

Such oil components may include, but are not limited to, the following. Liquid oils and fats include avocado oil, camellia oil, turtle oil, macadamia nut oil, corn oil, mink oil, olive oil, rapeseed oil, yolk oil, sesame oil, persic oil, wheat germ oil, sasanqua oil, castor oil, linseed oil, safflower oil, cottonseed oil, Perilla oil, soybean oil, peanut oil, tea seed oil, *Torreya nucifera* oil, rice-bran oil, Chinese tung oil, Japanese tung oil, jojoba oil, germ oil, triglycerin, glyceryl trioctanoate, pentaerythritol tetraoctanoate, and glyceryl triisopalmitate. Solid oils and fats include cacao oil, coconut oil, hydrogenated coconut oil, palm oil, palm kernel oil, Japan wax kernel oil, and hardened oils. Hydrocarbon oils include liquid paraffin, ozokerite, squalene, pristane, paraffin, and squalane.

The amount of the wax to be used in the present invention preferably ranges from 0.01 to 25 mass %, more preferably from 0.1 to 15 mass %, in the total amount of the finely dispersed wax composition. If the wax content is less than 0.01 mass %, it is difficult to obtain a skin-tension feeling after application. On the other hand, if the wax is used in an amount greater than 25 mass %, formulations are difficult to prepare.

<Nonionic Surfactant>

The nonionic surfactant is not particularly limited as long as it is of types that can generally be used in cosmetics, but in the present invention, it is preferred that the weight-averaged HLB for all the nonionic surfactants in the finely dispersed wax composition is in the range of 10-15, more preferably 11-14, and even more preferably 12-13. By using nonionic surfactants providing HLB values within the stated ranges, one can obtain such a clear composition that the wax has been solubilized in a hot state (e.g., within the solubilizing temperature range not lower than the melting point of the wax). HLB can be calculated by the Kawakami Equation represented by the following formula 1:

$$HLB = 7 + 11.7 \cdot \log(MW/MO) \quad \text{[Formula 1]}$$

(where MW represents the molecular weight of the hydrophilic moiety and MO represents the molecular weight of the lipophilic moiety).

In the present invention, the nonionic surfactant that may be used with particular preference is one or more substances selected from among POE alkyl ethers, POE-POP alkyl ethers, POE glyceryl ether fatty acid esters, and POE castor oil or POE hydrogenated castor oil and their derivatives. Among these substances, POE alkyl ethers and POE-POP alkyl ethers are particularly advantageous to use because the prepared fine dispersion of the wax has such good stability with time that the fine particles of the wax will not agglomerate or otherwise deteriorate over time to cause a change in appearance (lowered transparency) or creaming of the dispersed particles.

As will be described later in this specification, the finely dispersed wax composition which is used in the present invention is advantageously produced by a process comprising the steps of heating the system until the wax is solubilized and then cooling the system to ordinary temperatures so that the wax becomes finely dispersed. If one or more substances selected from between POE alkyl ethers and POE-POP alkyl ethers are used in combination with POE glyceryl ether fatty acid esters as nonionic surfactants, the rate of wax solubilization can be remarkably increased to achieve an improvement in production efficiency.

As the above-mentioned POE alkyl ethers and POE-POP alkyl ethers, one or more substances selected from among compounds represented by the following formulas (I) and/or (II) are preferably used:

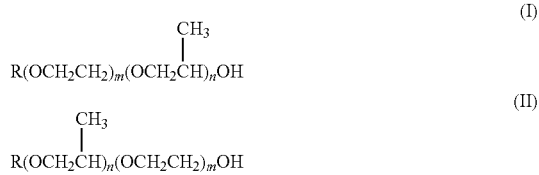

[in the formulas (I) and (II), R represents an alkyl or alkenyl group having 12-24 carbon atoms, m represents a number of 5-30, and n represents a number of 0-5].

Examples of the above-described POE alkyl ethers and POE-POP alkyl ethers include POE lauryl ethers, POE cetyl ethers, POE stearyl ethers, POE oleyl ethers, POE behenyl ethers, POE decyltetradecyl ethers, POE monobutyl ethers, POE 2-decyltetradecyl ethers, POE hydrogenated lanolin, POE glyceryl ethers, POE-POP lauryl ethers, POE-POP cetyl ethers, POE-POP stearyl ethers, POE-POP oleyl ethers, POE-POP behenyl ethers, POE-POP decyltetradecyl ethers, POE-POP monobutyl ethers, POE-POP 2-decyltetradecyl ethers, POE-POP hydrogenated lanolin, and POE-POP glyceryl ethers.

Examples of the above-mentioned POE glyceryl ether fatty acid esters include POE glyceryl ether monostearic acid ester, POE glyceryl ether monoisostearic acid ester, and POE glyceryl ether triisostearic acid ester.

Examples of the above-mentioned POE castor oil or POE hydrogenated castor oil and their derivatives include POE castor oil, POE hydrogenated castor oil, POE hydrogenated castor oil monoisostearate, POE hydrogenated castor oil triisostearate, POE hydrogenated castor oil monopyroglutamic acid monoisostearic acid diester, and POE hydrogenated castor oil maleate.

In the present invention, any nonionic surfactants other than those listed above can also be used, and examples include: POE sorbitan fatty acid esters, such as POE sorbitan monooleate and POE sorbitan tetraoleate; POE sorbitol fatty acid esters, such as POE sorbitol monolaurate, POE sorbitol monooleate, POE sorbitol pentaoleate, and POE sorbitol monostearate; POE fatty acid esters, such as POE monooleate and ethylene glycol distearate; POE alkylphenyl ethers, such as POE octylpyhenyl ether, POE nonylphenyl ether, and POE dinonylphenyl ether; pluronics such as pluronic; tetraPOE-tetraPOP ethylenediamine condensates such as Tetronic; POE beeswax-lanolin derivatives such as POE sorbitol beeswax; alkanol amides, such as coconut oil fatty acid diethanol amides, lauric acid monoethanol amide, and fatty acid isopropanol amides; as well as POE propylene glycol fatty acid esters, POE alkylamines, POE fatty acid amides, sucrose fatty acid esters, POE nonylphenyl formaldehyde condensate, alkylethoxydimethyl amine oxides, and trioleyl phosphate.

The proportion of the nonionic surfactant relative to the wax for use in the present invention is 1.0 or more (in mass ratio) in the total amount of the finely dispersed wax composition, with 1.1 or more being preferred. If this mass ratio is less than 1.0, a composition of high stability is difficult to obtain. The upper limit of the above-defined mass ratio is not particularly limited but it is preferably not greater than about 5.0, more preferably not greater than about 3.0. If the value of this mass ratio is unduly great, the feeling in use has a tendency to become worse.

<Aqueous Dispersion Medium>

Water may be used alone as the aqueous dispersion medium; alternatively, it may be used as liquid mixtures of water and other substances such as ethanol, glycerin, polyethylene glycol, propylene glycol, dipropylene glycol, 1,3-butanediol, xylitol, sorbitol, maltitol, chondroitin sulfate, mucoitin sulfate, calonic acid, atherocollagen, cholesteryl-12-hydroxystearate, sodium lactate, bile acid salts, short-chain soluble collagens, diglycerin(EO)PO adducts, chestnut rose extract, yarrow extract, and melilot extract.

In the present invention, the wax described earlier is dispersed as fine particles having a particle size of no more than 500 nm (=finely divided wax; microwax) in a solid or semisolid state in an aqueous solvent. In a system containing ultra fine particle size as fine as 500 nm or less (=microemulsion system), differing from an ordinary emulsion system of large particle size, is so stable that it is difficult to separate into two phases with a lapse of time. Such a stable microemulsion system can be obtained by incorporating larger amount of nonionic surfactant to wax (in the present invention, as mentioned above, the mass ratio of nonionic surfactant relative to wax was made 1.0 or higher), and further more preferably by heating the system to a temperature over the melting point of wax within the range of solubilizing temperature to form a solubilized state, and after that cooling to ordinary temperature, as mentioned below in detail in the section of <Process for Production>.

The term "solubilizing" is generally defined as stably and transparently dissolving a water-insoluble or hardly soluble material in a micell solution formed with an emulsifying agent; once wax is solubilized in a system under heating within the range of solubilizing temperature, followed by cooling; thus a stable wax dispersion of very fine particles of 500 nm or less in size as in the present invention can be produced more efficiently. The "solubilizing" phenomenon can also be accomplished by adding a large amount of nonionic surfactant relative to wax.

<Ionic Water-Soluble Thickeners>

The ionic water-soluble thickener used in the present invention includes alginate-type polymers, such as sodium alginate, and propylene glycol alginate; vinylic polymers, such as carboxyvinyl polymer, and alkyl-modified carboxyvinyl polymer; acrylic polymers, such as sodium polyacrylate, polyethyl acrylate, and polyacrylamide; polyethyleneimide; and cationic polymers, such as cationic cellulose, polydiallyldimethylammonium salt, diallyldimethylammonium salt/acrylamide copolymer, vinylpyrrolidone/dimethylaminoethyl methacrylate polymer, but not limited thereto. In particular, vinylic polymers, such as carboxyvinyl polymer, and alkyl-modified carboxyvinyl polymer, etc., are preferably used. The ionic water-soluble thickener may be used either alone or in combination.

The amount of the ionic water-soluble thickener to be used in the present invention is preferably ranges from 0.01 to 5 mass %, particularly from 0.1 to 2 mass %, in the total amount of the finely dispersed wax composition. When it is less than 0.01 massa, it is difficult to adjust the viscosity of the composition; on the other hand, when it is over 5 mass %, the feeling in use has a tendency to become worse.

In the present invention, ionic surfactants, i.e., anionic surfactants, cationic surfactants and amphoteric surfactants are substantially not contained. The phrase "substantially not contained" means that the case is excluded where these ionic surfactants are contained at the level of the content at which the effect of the surfactants as active ingredients is exhibited. In the absence of these ionic surfactants, the effect of the ionic water-soluble thickener (the effect affording a skin-tension feeling and improving the easiness of application topically to the skin with fingers to such as the corner of eye or the mouth and the like) is shown sufficiently.

<Silicone Oils and/or Fluorinated Oils>

In the present invention, in addition to the above-mentioned components, silicone oils and/or fluorinated oils which are liquid at ordinary temperature may be added.

The silicone oil being liquid at ordinary temperature used in the present invention includes chain silicones, such as dimethylpolysiloxane, methylphenylpolysiloxane, and methyl hydrogen polysiloxane; cyclic silicones, such as octamethylcyclotetrasiloxane, decamethylcyclopentasiloxane, and dodecamethylcyclohexanesiloxane; amino-modified silicone oil, polyether-modified silicone oil, carboxy-modified silicone oil, alkyl-modified silicone oil, ammonium salt-modified silicone oil, fluorinated-modified silicone oil, silicone resins forming a three-dimensional network such as trimethylsiloxy silicate; highly polymerized methylpolysiloxanes, such as highly polymerized dimethylpolysiloxane, highly polymerized methylphenylpolysiloxane, and highly polymerized methylvinylpolysiloxane; highly polymerized amino-modified methylpolysiloxane, and the like.

The fluorinated oil component being liquid at ordinary temperature used in the present invention includes perfluoropolyethers and the like. Commercially available one includes "FOMBLIN HC-04", "FOMBLIN HC-25", and "FOMBLIN HC-R" (made by Montefluos).

In the invention, one or more ones may be used from among the above-mentioned silicone oils and fluorinated oil components.

The ratio of the silicone oils or fluorinated oil components used in the present invention is preferably 0.1-10 mass %, particularly 1-5 mass % based on the total amount of the finely dispersed wax composition. When it is less than 0.1 mass %, the feeling of stickiness cannot be suppressed enough to a satisfactory level, and on the other hand, when it is over 10 mass %, the feeling in use has a tendency to become worse.

<Process for Production>

In the finely dispersed wax composition that is to be used in the present invention, the finely divided wax having a particle size of no more than 500 nm is dispersed in solid or semisolid form in the aqueous dispersion medium. The process for producing such a finely dispersed wax composition is not particularly limited but the following process may be given as an advantageous example.

1. Embodiment of a Finely Dispersed Wax Composition that does not Contain Silicone Oil and/or Fluorinated Oil In the process, a system containing wax, nonionic surfactant, and aqueous dispersion medium is heated to a temperature not lower than the melting point of the wax but within the solubilizing temperature range so that the system is rendered to a solubilized state and is thereafter cooled to ordinary temperatures, followed by adding an ionic water-soluble thickener thereinto. A more specific advantageous embodiment may be exemplified by the following: the nonionic surfactant and optionally a polyhydric alcohol are dissolved in ion-exchange water and to the solution being heated to 85-95° C., the wax (e.g., carnauba wax, etc.) is added and the resulting mixture is agitated with a propeller for a period of about 30 minutes to about 2 hours and after confirming the solubilized state of the said mixture, which is then ice-cooled, followed by adding the ionic water-soluble thickener into the solution and stirring it to make a finely dispersed wax composition. In this process, as mentioned earlier, one or more substances selected from between POE alkyl ethers and POE-POP alkyl ethers may be used in combination with POE glyceryl ether fatty acid esters as nonionic surfactants, whereupon the rate of wax solubilization can be remarkably increased to achieve an improvement in production efficiency. As a result, the finely divided wax is efficiently dispersed in the aqueous dispersion medium. Needless to say, the process for producing the finely dispersed wax composition is in no way limited to the conditions described in the foregoing specific example.

In addition to the production process described above, there is another method that may be employed to prepare the system containing the above-described wax, nonionic surfactant, and aqueous dispersion medium and this method can be performed by using a high-shear emulsifying machine at a temperature not lower than the melting point of the wax, and after that ionic water-soluble thickener is added to the solution with further emulsifying. In the case of using an emulsifying machine capable of imparting a strong shear force, for example, a high-pressure homogenizer, emulsification is preferably performed under a pressure of at least 400 atm but more preferably, it is performed at a temperature not lower than the melting point of the wax under a pressure of at least 600 atm.

2. Embodiment of a Finely Dispersed Wax Composition that Contains Silicone Oil and/or Fluorinated Oil In the process, a system containing wax, nonionic surfactant, and aqueous dispersion medium is heated to a temperature not lower than the melting point of the wax but within the solubilizing temperature range so that the system is rendered to a solubilized state and is thereafter cooled to ordinary temperatures, followed by adding an ionic water-soluble thickener and silicone oil and/or fluorinated oil thereinto. A more specific advantageous embodiment may be exemplified by the following: the nonionic surfactant and optionally a polyhydric alcohol are dissolved in ion-exchange water and to the solution being heated to 85-95° C., the wax (e.g., carnauba wax, etc.) is added and the resulting mixture is agitated with a propeller for a period of about 30 minutes to about 2 hours and after confirming the solubilized state of the said mixture, which is then ice-cooled, followed by adding the ionic water-soluble thickener and silicone oil and/or fluorinated oil into the solution and stirring it to make a finely dispersed wax composition. In this process, as mentioned earlier, one or more substances selected from between POE alkyl ethers and POE-POP alkyl ethers may be used in combination with POE glyceryl ether fatty acid esters as nonionic surfactants, whereupon the rate of wax solubilization can be remarkably increased to achieve an improvement in production efficiency. As a result, the finely divided wax is efficiently dispersed in the aqueous dispersion medium. Needless to say, the process for producing the finely dispersed wax composition is in no way limited to the conditions described in the foregoing specific example.

In addition to the production process described above, there is another method that may be employed to prepare the system containing the above-described wax, nonionic surfactant, and aqueous dispersion medium and this method can be performed by using a high-shear emulsifying machine at a temperature not lower than the melting point of the wax, and after that ionic water-soluble thickener and silicone oil and/or fluorinated oil are added to the solution with further emulsifying. In the case of using an emulsifying machine capable of imparting a strong shear force, for example, a high-pressure homogenizer, emulsification is preferably performed under a pressure of at least 400 atm but more preferably, it is performed at a temperature not lower than the melting point of the wax under a pressure of at least 600 atm.

[Skin External Preparation]

The skin external preparation of the present invention contains the finely dispersed wax composition described above.

In skin external preparations, it is generally difficult to obtain a cosmetic product having a high skin-tension feeling only by incorporating a water-soluble polymer thereinto. In the present invention, however, it became possible to obtain a skin external preparation having a high skin-tension feeling by incorporating a finely dispersed wax composition (=wax microdispersion composition) in which wax of 500 nm or less in particular size is dispersed in a solid or semisolid state. When a cosmetic product using an ordinary emulsion system of large particle size is applied to the skin, the wax might deposit sometimes on the skin with a lapse of time, but in the present invention, the use of a finely dispersed wax composition as mentioned above prevents the deposition of the wax on the skin with a lapse of time after application of the skin external preparation.

In general, it is difficult to stably disperse solid or semi-solid wax into water, but in the present invention, the use of a certain surfactant, and furthermore as a preferred embodiment the adoption of a specific production process, can afford a highly stable finely dispersed wax composition which gives a high skin-tension feeling.

Further, ionic surfactants are worried about safety. In this regard, in the present invention, it was possible to solubilize wax without incorporating any ionic surfactants in the skin external preparations. Since no ionic surfactants are used in the present invention, it was possible to increase the viscosity by virtue of an ionic polymer and to greatly improve the skin-tension feeling after application to the skin. It was also possible to improve the easiness of application topically to the skin such as the corner of eye or the mouth and the like. In addition, by the incorporation of a silicone oil and/or fluorinated oil component, it was possible to obtain an excellent applicability to the skin with no-stickiness, and adhesiveness to the skin in addition to the above-mentioned effects.

Besides the finely dispersed wax composition of the present invention, ingredients that may be commonly added to skin external preparations and other cosmetics may be added, as appropriate for the need, to the skin external preparation of the present invention. Such optional additive ingredients include humectants such as polyhydric alcohols (e.g., glycerin), perfumes, pH modifiers, antiseptics, various kinds of powders, oil-soluble drugs (e.g., Vitamin A, etc.), and water-soluble thickener except of the above-mentioned ionic water-soluble thickeners, but are not limited thereto.

The skin external preparation of the present invention can advantageously be used as various products that are specifically exemplified by lotions, beauty essences in lotion form, beauty essences in jelly form, skin-care creams, and impregnated mask of nonwoven fabric. Advantageous dosage forms may be exemplified by but are not limited to clear to semiclear, finely dispersed lotions and thickened jelly products.

EXAMPLES

The present invention is hereunder described in greater detail by means of the following Examples which are by no means intended to limit the invention. Unless otherwise noted, the amounts in which various components are incorporated are indicated by mass % relative to the system to which they are added.

1. Embodiment of a Finely Dispersed Wax Composition that does not Contain Silicone Oil and/or Fluorinated Oil Example 1: Optimum HLB for the Nonionic Surfactant In the basic formula II shown below, the HLB of nonionic surfactants was varied as shown in Table 1 and the state of dispersion (appearance) of the resulting systems was examined to determine optimum HLB values for the nonionic surfactants used.

| <Basic formula 1> | |
|---|---|
| Carnauba wax | 10 mass % |
| Carboxyvinyl polymer | 0.3 mass % |
| Potassium hydroxide | 0.1 mass % |

-continued

| <Basic formula 1> | |
|---|---|
| Nonionic surfactant (See Table 1) | 13.5 mass % |
| Ion-exchange water | bal. |
| Total | 100 mass % |

(Test Method)

Finely dispersed wax compositions of the basic formula 1 above were prepared. To be more specific, the nonionic surfactant (Table 1) was dissolved in ion-exchange water and to the solution being heated to 85-95° C., carnauba wax was added and the resulting mixture was agitated with a propeller for about 2 hours. Thereafter, the mixture was ice-cooled to prepare the intermediate composition. These intermediate compositions were allowed to stand at room temperature for an hour and visually observed for their appearance (state of dispersion). The results are also shown in Table 1.

TABLE 1

| Nonionic surfactant in <Basic formula 1> | Amount (mass %) | HLB | State of dispersion | Average particle size of wax |
|---|---|---|---|---|
| POE(10)behenyl ether | 13.5 | 9 | Phase Separation occurred. | — |
| POE(10)behenyl ether<br>POE(50)lauryl ether | 12.49<br>1.01 | 10 | Creamy | 380 nm |
| POE(10)behenyl ether<br>POE(50)lauryl ether | 11.14<br>2.36 | 11 | Semiclear one-liquid phase | 90 nm |
| POE(15)behenyl ether | 13.5 | 12 | Clear one-liquid phase | 46 nm |
| POE(20)behenyl ether | 13.5 | 13 | Clear one-liquid phase | 35 nm |
| POE(20)behenyl ether<br>POE(30)lauryl ether | 6.75<br>6.75 | 14 | Semiclear one-liquid phase | 46 nm |
| POE(30)behenyl ether | 13.5 | 15 | Creamy | 290 nm |

As is clear from the data in Table 1, uniform dispersion systems could be formed with nonionic surfactants having HLB values of at least 10 but not more than 15. It was also confirmed that clear (=transparent) to semiclear (=semi-transparent) systems of one-liquid phase were obtained with nonionic surfactants having HLB values of 11 to 14 and that, in particular, HLB values of 12 to 13 were required to obtain clear systems.

After that, a carboxyvinyl polymer was added to these intermediate compositions and stirred with a propeller for about an hour to dissolve the polymer, to which was added potassium hydroxide to yield the final compositions. The HLB of the final composition was the same as that of the intermediate compositions, and almost no change was observed in appearance. The average particle size of the wax fine particles contained in the final composition was measured. The results are also shown in Table 1. The particle size was measured as follows.

That is, each of the final compositions was diluted to one-tenth with ion-exchange water to prepare a sample. These samples were observed with a "Zetasizer Nano Series NANO-ZS" (Sysmex Corp.) to measure the particle size of wax.

Example 2: Types of Nonionic Surfactants and the State of Dispersion of the Resulting Systems In the above-mentioned basic formula 1, POE straight-chain alkyl ethers or POE branched-chain alkyl ethers were used as nonionic surfactants as shown in Table 2 below, and their HLB values were varied between 9 and 15 by changing the number of moles ("n") of adducts in POE; the state of dispersion of the respective systems was evaluated by the criterion defined below. The results are shown in Table 2.

(Test Method)

The nonionic surfactant (Table 2) was dissolved in ion-exchange water and to the solution being heated to 85-95° C., carnauba wax was added and the resulting mixture was agitated with a propeller for about 2 hours. Thereafter, the mixture was ice-cooled to prepare intermediate compositions. These intermediate compositions were allowed to stand at room temperature for an hour and visually observed for their appearance. The results are also shown in Table 2.

(Evaluation)

○: A clear one-liquid phase formed.
Δ: A semiclear or uniform creamy appearance was seen.
x: Phase separation occurred.

TABLE 2

| Nonionic surfactant in <Basic formula 1> | HLB value | | | | | | |
|---|---|---|---|---|---|---|---|
| | 9 | 10 | 11 | 12 | 13 | 14 | 15 |
| POE straight-chain alkyl ether | | | | | | | |
| C12 (lauryl) | X<br>n = 5 | Δ<br>n = 7 | | | | ○<br>n = 15 | |
| C16 (cetyl) | X<br>n = 7 | | Δ<br>n = 9 | | | | |
| C18 (stearyl) | X<br>n = 8 | Δ<br>n = 10 | | ○<br>n = 15 | | Δ<br>n = 20 | |
| C18 (oleyl) | X<br>n = 8 | Δ<br>n = 10 | | ○<br>n = 15 | | | |
| C20 (aralkyl) | X<br>n = 10 | | | | ○<br>n = 18 | | |
| C22 (behenyl) | X<br>n = 10 | | | ○<br>n = 15 | ○<br>n = 20 | | Δ<br>n = 30 |
| POE branched-chain alkyl ether | | | | | | | |
| C18 (isostearyl) | | Δ<br>n = 10 | | ○<br>n = 15 | ○<br>n = 20 | | |
| C20 (octyldodecyl) | | Δ | | ○ | ○ | | |

TABLE 2-continued

| Nonionic surfactant in <Basic formula 1> | HLB value 9 | 10 | 11 | 12 | 13 | 14 | 15 |
|---|---|---|---|---|---|---|---|
| C24 (decyltetradecyl) | X (n=10) | n=10 | Δ (n=15) | ○ (n=16, n=20) | n=20 | Δ (n=15) | |
| POE(20) glyceryl ether isostearic acid ester | | | | ○ (n=20) | | | ○ (n=60) |
| Combination of POE(20) glyceryl ether isostearic acid ester and POE(20) straight-chain behenyl alkyl ether | | | | ○ (n=20) | | | |

(n: Number of moles of adducts in POE)

As is clear from the data in Table 2, when the respective nonionic surfactants were used independently, clear systems of one-liquid phase could be formed by adjusting their HLB values to lie at approximately 12-13. It was also confirmed that a plurality of nonionic surfactants could be used in combination.

A carboxyvinyl polymer was added to these intermediate compositions and stirred with a propeller for about an hour to dissolve the polymer, to which was added potassium hydroxide to yield the final compositions (=finely dispersed wax compositions). The HLB of the final composition was the same as that of the intermediate composition, and almost no change was observed in appearance.

The average particle size of wax fine particles contained in the final composition was measured in the same manner as in Example 1. The dispersion state as results was evaluated as follows: In the evaluation of "○: A clear one-liquid phase formed.", average particle size is 20-49 nm; in the evaluation of "Δ: A semiclear or uniform creamy appearance was seen.", average particle size is 50-400 nm; and in the evaluation of "x: Phase separation occurred.", the average particle size could not be measured.

Example 3: Stability with Time

In the basic formula 2 shown below, the nonionic surfactant was varied as shown in Table 3 below and the stability of the resulting systems was evaluated by the criterion defined below.

| <Basic formula 2> | |
|---|---|
| Carnauba wax | 10 mass % |
| Nonionic surfactant (See under Table 3) | 15 mass % |
| Alkyl-modified carboxyvinyl polymer | 0.05 mass % |
| Ion-exchange water | bal. |
| Total | 100 mass % |

(Test Method)

The surfactant was dissolved in ion-exchange water and to the solution being heated to 85-95° C. carnauba wax was added and the resulting mixture was agitated with a propeller for about 2 hours. Thereafter, the mixture was ice-cooled, and then the alkyl-modified carboxyvinyl polymer was added thereinto to prepare final compositions (=finely dispersed wax compositions), which were clear and of one-liquid phase.

The compositions (samples 1 to 6) were allowed to stand at 50° C. for a week, visually observed for their state, and had their stability with time evaluated by the criterion defined below. The results are also shown in Table 3.

(Evaluation)

○: No change from the state of the as-prepared sample.

x: Phase separation occurred.

TABLE 3

| | Sample | | | | | |
|---|---|---|---|---|---|---|
| | 1 | 2 | 3 | 4 | 5 | 6 |
| Carnauba wax | 10 | 10 | 10 | 10 | 10 | 10 |
| POE(10) behenyl ether | 5 | — | — | — | — | 12 |
| POE(15) behenyl ether | — | 12 | 10 | 5 | — | — |
| POE(20) behenyl ether | — | 12 | — | 7 | 9 | 9 |
| POE(30) behenyl ether | — | — | — | 7 | — | — |
| POE(40) hydrogenated castor oil | 10 | — | — | — | — | — |
| POE(20) glyceryl ether isostearic acid ester | — | — | — | — | — | 6.5 |
| POE(4.5) lauryl acetate ether (ca. 20 mass % effective content) | — | — | 1.5 | 7.5 | — | — |
| Alkyl-modified carboxyvinyl polymer | 0.5 | 0.5 | 0.5 | 0.5 | 0.5 | 0.5 |
| Ion-exchange water | bal. | bal. | bal. | bal. | bal. | bal. |
| Stability | ○ | ○ | ○ | ○ | X | ○ |
| Average particle size of wax (nm) | 38 | 35 | 42 | 27 | — | 29 |

As is clear from the data shown in Table 3, sample 5 in which the mass ratio of the nonionic surfactant to the wax was less than unity experienced phase separation and failed to exhibit good stability.

Example 4 and Comparative Example 1: Solubilizing Rate of Wax

According to Table 4 shown below, a surfactant or surfactants and dipropylene glycol were dissolved in ion-exchange water, and to the solution being heated to 85-95° C., carnauba wax added and the resulting mixture was agitated with a propeller and the time it took for the carnauba wax to be solubilized was measured. The results are also shown in Table 4. Thusly prepared solubilized intermediate compositions above were ice-cooled, and then the alkyl-modified carboxyvinyl polymer was added thereinto to prepare final compositions (=finely dispersed wax compositions).

TABLE 4

|  | Example 4 | Comparative Example 1 |
|---|---|---|
| Carnauba wax | 10 | 10 |
| POE(20)behenyl ether | 12 | 18 |
| POE(20)glyceryl ether isostearic acid ester | 6 | — |
| Dipropylene glycol | 6 | 6 |
| Alkyl-modified carboxyvinyl polymer | 0.2 | 0.2 |
| Ion-exchange water | bal. | bal. |
| Time to wax solubilization (min) | 30 | 60 |

As is clear from the data in Table 4, the time it took for the wax to become solubilized in Example 4 where POE(20)behenyl ether and POE(20)glyceryl ether isostearic acid ester were used in combination as nonionic surfactants could be made considerably shorter than in Comparative Example 1 which used only one kind of nonionic surfactant, i.e., POE(20)behenyl ether. A particle size of the finely divided wax each in Example 4 and Comparative Example 1 was 20-49 nm.

Example 5: Feeling in Use

According to the process for production as described in Example 1, a sample comprising the following components was heated, solubilized and cooled to give a stock solution (=finely dispersed wax solution) for impregnated mask. The size of fine wax particles in the resulting stock solution was 28 nm. This stock solution was impregnated in nonwoven fabric to prepare an impregnated mask of nonwoven fabric (product of the invention).

<Stock Solution for Impregnated Mask>

| <Compound component> | (mass %) |
|---|---|
| Carnauba wax | 0.3 |
| POE(20)behenyl ether | 0.3 |
| POE(20)glyceryl ether isostearic acid ester | 0.2 |
| POE-POP decyltetradecyl ether | 0.2 |
| Glycerin | 3 |
| Btylene glycol | 10 |
| Dipropylene glycol | 5 |
| Phenoxyethanol | 0.5 |
| Carboxyvinyl polymer | 0.1 |
| Trisodium edetate | 0.02 |
| Ethanol | 3 |
| Potassium hydroxide | q.s. |
| Perfume | q.s. |
| Ion-exchange water | bal. |

<Test Method>

As for the feeling in use as shown in Table 5, it was evaluated by 31 panelists who have usually used a commercially available impregnate-type mask of nonwoven fabric. That is, the above-mentioned impregnated mask of nonwoven fabric (product of the invention) was compared to commercially available ordinary masks (impregnated masks usually used by the panelists) for the actual feeling in use according to the following evaluations. The results are also shown in Table 5. The stock solution was superior in stability.

<Evaluations>
+2: the mask of the invention is much better than ordinary one.
+1: the mask of the invention is better than ordinary one.
0: the mask of the invention is comparable to ordinary one.
−1: the ordinary product is better than the product of the invention.
−2: the ordinary product is much better than the product of the invention.

TABLE 5

| Feeling in use | Evaluations | | | | |
|---|---|---|---|---|---|
|  | +2 | +1 | 0 | −1 | −2 |
| Seems occurrence of skin-tension feeling | 8 panelists | 13 panelists | 6 panelists | 4 panelists | 0 panelists |
| Good penetration of the liquid into the skin | 5 panelists | 5 panelists | 19 panelists | 2 panelists | 0 panelists |
| Moist feeling of the skin | 5 panelists | 12 panelists | 8 panelists | 5 panelists | 1 panelist |
| Bouncy feeling of the skin | 7 panelists | 10 panelists | 12 panelists | 2 panelists | 0 panelists |
| Soft feeling of the skin | 4 panelists | 8 panelists | 15 panelists | 4 panelists | 0 panelists |
| Strong skin-tension feeling | 6 panelists | 16 panelists | 5 panelists | 4 panelists | 0 panelists |
| Highly satisfied care with a mask | 10 panelists | 9 panelists | 7 panelists | 5 panelists | 0 panelists |

As clearly seen from the results in Table 5, the product of Example 5 (product of the invention) is particularly superior in skin-tension feeling, allowing to provide an impregnated mask giving high satisfaction for skin care.

Set forth below are formulae that can be applied in the present invention.

[Compounding formula 1: Beauty lotion]

| (Ingredients to be compounded) | (mass %) |
|---|---|
| (1) Carnauba wax | 1.5 |
| (2) POE(20)behenyl ether | 1.8 |
| (3) Carboxyvinyl polymer | 0.3 |
| (4) Potassium hydroxide | 0.1 |
| (5) Tocopherol acetate | 0.05 |
| (6) Glycerin | 5 |
| (7) Ion-exchange water | bal. |
| (8) Perfume | q.s. |
| (9) Phenoxyethanol | 0.5 |

(Method of Production)

Ingredients (1), (2), (5) and (8), as well as portions of ingredients (6) and (7) were mixed under stirring at about 95° C. until the mixture became clear; thereafter, it was ice-cooled to make a fine dispersion of the wax; the fine dispersion of the wax was added to a mixture of the remaining portions of (6) and (7) with a mixture of ingredients (3), (4) and (9) to make a beauty lotion.

[Compounding formula 2: Skin-lightening jelly]

| (Ingredients to be compounded) | (mass %) |
|---|---|
| (1) Carnauba wax | 0.5 |
| (2) Candelilla wax | 0.3 |
| (3) Rice wax | 0.2 |
| (4) Beeswax | 0.1 |
| (5) Microcrystalline wax | 0.1 |

[Compounding formula 2: Skin-lightening jelly] (continued)

| (Ingredients to be compounded) | (mass %) |
|---|---|
| (6) Paraffin wax | 0.1 |
| (7) Petrolatum | 0.1 |
| (8) Behenyl alcohol | 0.1 |
| (9) Stearyl alcohol | 0.03 |
| (10) POE(10)behenyl ether | 0.1 |
| (11) POE(20)behenyl ether | 1.5 |
| (12) POE(30)behenyl ether | 0.1 |
| (13) POE(20)glyceryl ether isostearic acid ester | 0.1 |
| (14) Retinol palmitate | 0.01 |
| (15) α-Tocopherol | 0.01 |
| (16) Tetraisopalmitoylascorbyl | 0.01 |
| (17) Isobutyl resorcine | 0.01 |
| (18) Linoleic acid | 0.03 |
| (19) Linolenic acid | 0.02 |
| (20) Ascorbic acid phosphate sodium salt | 0.01 |
| (21) Ascorbic acid phosphate magnesium salt | 0.01 |
| (22) Ascorbic acid 2-glucoside | 2 |
| (23) Ethyl ascorbate | 0.01 |
| (24) Pantothenylethyl ether | 0.01 |
| (25) Arbutin | 0.01 |
| (26) Methyl tranexamate amide salt | 1 |
| (27) Dipotassium glycyrrhizinate | 0.01 |
| (28) 4-Methoxysalicylic acid salt | 1 |
| (29) Glycerin | 1 |
| (30) Dipropylene glycol | 10 |
| (31) Polyoxyethylene glycol | 1 |
| (32) Paraoxybenzoic acid ester | 0.15 |
| (33) Phenoxyethanol | 0.3 |
| (34) Trisodium edentate | 0.02 |
| (35) Citric acid | q.s. |
| (36) Sodium citrate | q.s. |
| (37) Potassium hydroxide | q.s. |
| (38) Carboxyvinyl polymer | 0.2 |
| (39) Acrylic acid/alkyl(C$_{10-30}$) acrylate copolymer | 0.5 |
| (40) Hydroxyethyl cellulose | 0.1 |
| (41) Methyl cellulose | 1 |
| (42) 2-Methacryloyloxyethylphosphorylcholine/butyl methacrylate copolymer | 0.1 |
| (43) Ethanol | 10 |
| (44) Perfume | q.s. |
| (45) Ion-exchange water | bal. |

[Compounding formula 3: Moisturizing jelly]

| (Ingredients to be compounded) | (mass %) |
|---|---|
| (1) Carnauba wax | 0.5 |
| (2) Rice wax | 0.4 |
| (3) Paraffin wax | 0.1 |
| (4) POE cholesterol ether | 0.1 |
| (5) Glyceryl stearate | 0.05 |
| (6) Hydrogenated castor oil | 0.1 |
| (7) Behenyl alcohol | 0.2 |
| (8) Batyl alcohol | 0.05 |
| (9) Stearic acid | 0.05 |
| (10) Triglycerin | 0.05 |
| (11) Glycerol Trioctanoate | 0.05 |
| (12) Paraffin | 0.1 |
| (13) POE(10)behenyl ether | 0.7 |
| (14) POE(30)behenyl ether | 0.8 |
| (15) POP(1)POE(15)behenyl ether | 0.2 |
| (16) POE(20)glyceryl ether isostearic acid ester | 0.01 |
| (17) POE(60) hydrogenated castor oil | 0.5 |
| (18) Tocopherol acetate | 0.01 |
| (19) Stearyl glycyrrhetinate | 0.01 |
| (20) Ubiquinone | 0.01 |
| (21) β-Carotene | 0.01 |
| (22) Vitamin D$_2$ (= ergocalciperol) | 0.005 |
| (23) γ-Orizanol | 0.01 |
| (24) Ascorbic acid phosphate magnesium salt | 1 |
| (25) Nicotinic acid | 0.01 |
| (26) Urea | 2 |
| (27) Hyaluronic acid | 0.001 |
| (28) Acetylated hyaluronic acid | 0.001 |
| (29) Trehalose | 1 |
| (30) Erythritol | 1 |
| (31) Xylitol | 1 |
| (32) Glycerin | 5 |
| (33) Polyoxyethylene glycol | 5 |
| (34) POE-POP dimethyl ether | 1 |
| (35) Phenoxyethanol | 0.5 |
| (36) Trisodium edentate | 0.02 |
| (37) Citric acid | q.s. |
| (38) Sodium citrate | q.s. |
| (39) Potassium hydroxide | q.s. |
| (40) Behenyl alcohol | 0.1 |
| (41) Dimethyl acrylamide/sodium acryloyldimethyl taurate crosspolymer | 0.1 |
| (42) Perfume | q.s. |
| (43) Ion-exchange water | bal. |

[Compounding formula 4: UV preventing jelly]

| (Ingredients to be compounded) | (mass %) |
|---|---|
| (1) Carnauba wax | 0.4 |
| (2) Beeswax | 0.5 |
| (3) Paraffin wax | 0.1 |
| (4) POE cholesterol ether | 0.1 |
| (5) Hydrogenated castor oil | 0.1 |
| (6) Behenyl alcohol | 0.5 |
| (7) Batyl alcohol | 0.1 |
| (8) Stearic acid | 0.05 |
| (9) Triglycerin | 0.05 |
| (10) Pentaerythritol tetraoctanoate | 0.1 |
| (11) POE(20)behenyl ether | 1.8 |
| (12) POE(20)glyceryl ether isostearic acid ester | 1.5 |
| (13) POE(60)glyceryl ether isostearic acid ester | 0.03 |
| (14) Tocopherol acetate | 0.01 |
| (15) Stearyl glycyrrhetinate | 0.01 |
| (16) Isobutyl resorcine | 0.01 |
| (17) Octocrylene | 0.05 |
| (18) Octyl methoxycinnamate | 0.05 |
| (19) Tranexamic acid | 1 |
| (20) Methyl tranexamate amide salt | 1 |
| (21) Nicotinic acid amide | 0.01 |
| (22) Hydroxyproline | 0.01 |
| (23) Glycerin | 10 |
| (24) Butylene glycol | 5 |
| (25) Polyoxyethylene glycol | 1 |
| (26) POE-POP dimethyl ether | 5 |
| (27) Paraoxybenzoic acid ester | 0.1 |
| (28) Phenoxyethanol | 0.5 |
| (29) Trisodium edentate | 0.02 |
| (30) Citric acid | q.s. |
| (31) Sodium citrate | q.s. |
| (32) Potassium hydroxide | q.s. |
| (33) Carboxyvinyl polymer | 0.5 |
| (34) Acrylic acid/alkyl(C$_{10-30}$) acrylate copolymer | 0.5 |
| (35) Ethanol | 5 |
| (36) Perfume | q.s. |
| (37) Ion-exchange water | bal. |

2. Embodiment of a Finely Dispersed Wax Composition that Contains Silicone Oil and/or Fluorinated Oil Example 6: Optimum HLB for the Nonionic Surfactant In the basic formula 3 shown below, the HLB of nonionic surfactants was varied as shown in Table 6 and the state of dispersion (appearance) of the resulting systems was examined to determine optimum HLB values for the nonionic surfactants used.

| <Basic formula 3> | |
|---|---|
| Carnauba wax | 10 mass % |
| Carboxyvinyl polymer | 0.3 mass % |
| Potassium hydroxide | 0.1 mass % |
| Nonionic surfactant (See Table 6) | 13.5 mass % |
| Dimethyl polysiloxane | 5.0 mass % |
| Ion-exchange water | bal. |
| Total | 100 mass % |

(Test Method)

Finely dispersed wax compositions of the basic formula 3 above were prepared. To be more specific, the nonionic surfactant (Table 6) was dissolved in ion-exchange water and to the solution being heated to 85-95° C., carnauba wax was added and the resulting mixture was agitated with a propeller for about 2 hours. Thereafter, the mixture was ice-cooled to prepare the intermediate composition. These intermediate compositions were allowed to stand at room temperature for an hour and visually observed for their appearance (state of dispersion). The results are also shown in Table 6.

TABLE 6

| Nonionic surfactant in <Basic formula 3> | Amount (mass %) | HLB | State of dispersion | Average particle size of wax (nm) |
|---|---|---|---|---|
| POE(10)behenyl ether | 13.5 | 9 | Phase Separation occurred. | — |
| POE(10)behenyl ether<br>POE(50)lauryl ether | 12.49<br>1.01 | 10 | Creamy | 380 |
| POE(10)behenyl ether<br>POE(50)lauryl ether | 11.14<br>2.36 | 11 | Semiclear one-liquid phase | 90 |
| POE(15)behenyl ether | 13.5 | 12 | Clear one-liquid phase | 46 |
| POE(20)behenyl ether | 13.5 | 13 | Clear one-liquid phase | 35 |
| POE(20)behenyl ether<br>POE(30)lauryl ether | 6.75<br>6.75 | 14 | Semiclear one-liquid phase | 46 |
| POE(30)behenyl ether | 13.5 | 15 | Creamy | 290 |

As is clear from the data in Table 6, uniform dispersion systems could be formed with nonionic surfactants having HLB values of at least 10 but not more than 15. It was also confirmed that clear (=transparent) to semiclear (=semitransparent) systems of one-liquid phase were obtained with nonionic surfactants having HLB values of 11 to 14 and that, in particular, HLB values of 12 to 13 were required to obtain clear systems.

After that, a carboxyvinyl polymer was added to these intermediate compositions and stirred with a propeller for about an hour to dissolve the polymer, to which was added potassium hydroxide, then added dimethyl polysiloxane, and thereafter homogenized them to yield the final compositions. The HLB of the final composition was the same as that of the intermediate compositions, and no change was observed in appearance from the point of uniformity of the composition systems, although transparency of the final composition was a little declined than that of the intermediate composition. The average particle size of the wax fine particles contained in the final composition was measured. The results are also shown in Table 5. The particle size was measured as the same way as described in Example 1.

Example 7: Types of Nonionic Surfactants and the State of Dispersion of the Resulting Systems In the above-mentioned basic formula 3, POE straight-chain alkyl ethers or POE branched-chain alkyl ethers were used as nonionic surfactants as shown in Table 7 below, and their HLB values were varied between 9 and 15 by changing the number of moles ("n") of adducts in POE; the state of dispersion of the respective systems was evaluated by the criterion defined below. The results are shown in Table 7.

(Test Method)

The nonionic surfactant (Table 7) was dissolved in ion-exchange water and to the solution being heated to 85-95° C., carnauba wax was added and the resulting mixture was agitated with a propeller for about 2 hours. Thereafter, the mixture was ice-cooled to prepare intermediate compositions. These intermediate compositions were allowed to stand at room temperature for an hour and visually observed for their appearance. The results are also shown in Table 7.

(Evaluation)

○: A clear one-liquid phase formed.
Δ: A semiclear or uniform creamy appearance was seen.
x: Phase separation occurred.

TABLE 7

| Nonionic surfactant in <Basic formula 3> | HLB value | | | | | | |
|---|---|---|---|---|---|---|---|
| | 9 | 10 | 11 | 12 | 13 | 14 | 15 |
| POE straight-chain alkyl ether | | | | | | | |
| C12 (lauryl) | X<br>n = 5 | Δ<br>n = 7 | | | | ○<br>n = 15 | |
| C16 (cetyl) | X<br>n = 7 | | Δ<br>n = 9 | | | | |
| C18 (stearyl) | X<br>n = 8 | Δ<br>n = 10 | | | ○<br>n = 15 | Δ<br>n = 20 | |
| C18 (oleyl) | X<br>n = 8 | Δ<br>n = 10 | | | ○<br>n = 15 | | |
| C20 (aralkyl) | X<br>n = 10 | | | | | ○<br>n = 18 | |
| C22 (behenyl) | X<br>n = 10 | | | | ○<br>n = 15 | ○<br>n = 20 | Δ<br>n = 30 |
| POE branched-chain alkyl ether | | | | | | | |

TABLE 7-continued

| Nonionic surfactant in <Basic formula 3> | HLB value | | | | | | |
|---|---|---|---|---|---|---|---|
| | 9 | 10 | 11 | 12 | 13 | 14 | 15 |
| C18 (isostearyl) | | Δ n = 10 | | ○ n = 15 | ○ n = 20 | | |
| C20 (octyldodecyl) | | Δ n = 10 | | ○ n = 16 | ○ n = 20 | | |
| C24 (decyltetradecyl) | X n = 10 | | Δ n = 15 | ○ n = 20 | | Δ n = 15 | |
| POE(20) glyceryl ether isostearic acid ester | | | | | ○ n = 20 | | ○ n = 60 |
| Combination of POE(20) glyceryl ether isostearic acid ester and POE(20) straight-chain behenyl alkyl ether | | | | | ○ n = 20 | | |

(n: Number of moles of adducts in POE)

As is clear from the data in Table 7, when the respective nonionic surfactants were used independently, clear systems of one-liquid phase could be formed by adjusting their HLB values to lie at approximately 12-13. It was also confirmed that a plurality of nonionic surfactants could be used in combination.

A carboxyvinyl polymer was added to these intermediate compositions and stirred with a propeller for about an hour to dissolve the polymer, to which was added potassium hydroxide, then added dimethyl polysiloxane, and thereafter homogenized them to yield the final compositions. The HLB of the final composition was the same as that of the intermediate compositions, and no change was observed in appearance from the point of uniformity of the composition systems, although transparency of the final composition was a little declined than that of the intermediate composition.

The average particle size of wax fine particles contained in the final composition was measured in the same manner as in Example 1. The dispersion state as results was evaluated as follows: In the evaluation of "○: A clear one-liquid phase formed.", average particle size is 20-49 nm; in the evaluation of "Δ: A semiclear or uniform creamy appearance was seen.", average particle size is 50-400 nm; and in the evaluation of "x: Phase separation occurred.", the average particle size could not be measured.

Example 8: Stability with Time

In the basic formula 4 shown below, the nonionic surfactant was varied as shown in Table 8 below and the stability of the resulting systems was evaluated by the criterion defined below.

| <Basic formula 4> | |
|---|---|
| Carnauba wax | 10 mass % |
| Nonionic surfactant (See under Table 3) | 15 mass % |
| Alkyl-modified carboxyvinyl polymer | 0.05 mass % |
| Dimethyl polysiloxane | 5 mass % |
| Ion-exchange water | bal. |
| Total | 100 mass % |

(Test Method)

The nonionic surfactant was dissolved in ion-exchange water and to the solution being heated to 85-95° C. carnauba wax was added and the resulting mixture was agitated with a propeller for about 2 hours. Thereafter, the mixture was ice-cooled, and then the alkyl-modified carboxyvinyl polymer, and silicone oil and/or fluorinated oil was added thereinto, the resulting composition was agitated with a propeller, followed by homogenized them to prepare finely dispersed wax compositions (=final compositions), which were clear and of one-liquid phase.

The compositions (samples 7 to 12) were allowed to stand at 50° C. for a week, visually observed for their state, and had their stability with time evaluated by the criterion defined below. The results are also shown in Table 8.

(Evaluation)
○: No change from the state of the as-prepared sample.
x: Phase separation occurred.

TABLE 8

| | Sample | | | | | |
|---|---|---|---|---|---|---|
| | 7 | 8 | 9 | 10 | 11 | 12 |
| Carnauba wax | 10 | 10 | 10 | 10 | 10 | 10 |
| POE(10) behenyl ether | 5 | — | — | — | — | 12 |
| POE(15) behenyl ether | — | 12 | 10 | 5 | — | — |
| POE(20) behenyl ether | — | 12 | — | 7 | 9 | 9 |
| POE(30) behenyl ether | — | — | — | 7 | — | — |
| POE(40) hydrogenated castor oil | 10 | — | — | — | — | — |
| POE(20) glyceryl ether isostearic acid ester | — | — | — | — | — | 6.5 |
| POE(4.5) lauryl acetate ether (ca. 20 mass % effective content) | — | — | 1.5 | 7.5 | — | — |
| Alkyl-modified carboxyvinyl polymer | 0.05 | 0.05 | 0.05 | 0.05 | 0.05 | 0.05 |
| Dimethyl polysiloxane | 5 | 5 | 5 | 5 | 5 | 5 |
| Ion-exchange water | bal. | bal. | bal. | bal. | bal. | bal. |
| Stability | ○ | ○ | ○ | ○ | X | ○ |
| Average particle size of wax (nm) | 38 | 35 | 42 | 27 | — | 29 |

As is clear from the data shown in Table 8, sample 11 in which the mass ratio of the nonionic surfactant to the wax was less than unity experienced phase separation and failed to exhibit good stability.

Example 9 and Comparative Example 2: Solubilizing Rate of Wax

According to Table 9 shown below, a surfactant or surfactants and dipropylene glycol were dissolved in ion-exchange water, and to the solution being heated to 85-95°

C., carnauba wax added and the resulting mixture was agitated with a propeller and the time it took for the carnauba wax to be solubilized was measured. The results are also shown in Table 9. Thusly prepared solubilized intermediate compositions above were ice-cooled, and then carboxyvinyl polymer was dissolved thereinto, followed by adding dimethyl polysiloxane, and homogenized them to prepare final compositions (=finely dispersed wax compositions).

TABLE 9

|  | Example 9 | Comparative Example 2 |
|---|---|---|
| Carnauba wax | 10 | 10 |
| POE(20)behenyl ether | 12 | 18 |
| POE(20)glyceryl ether isostearic acid ester | 6 | — |
| Dipropylene glycol | 6 | 6 |
| Carboxyvinyl polymer | 0.3 | 0.3 |
| Dimethyl polysiloxane | 5 | 5 |
| Ion-exchange water | bal. | bal. |
| Time to wax solubilization (min) | 30 | 60 |

As is clear from the data in Table 9, the time it took for the wax to become solubilized in Example 9 where POE(20)behenyl ether and POE(20)glyceryl ether isostearic acid ester were used in combination as nonionic surfactants could be made considerably shorter than in Comparative Example 2 which used only one kind of nonionic surfactant, i.e., POE(20)behenyl ether. A particle size of the finely dispersed wax each in Example 9 and Comparative Example 2 is 20-50 nm.

Examples 10-12; Comparative Examples 3-4

Skin-Tension Feeling; Adhesiveness; No-Sticky Feeling

Samples of the components as shown in Table 10 below were prepared (Examples 10-12; Comparative Examples 3-4), and applied to the skin to evaluate skin-tension feeling, adhesiveness to the skin, and no stickiness by 10 expert panelists according to the following criteria. The results are shown in Table 10. The products in Examples 10-12 and Comparative Examples 3-4 all had good stability.

<Evaluation of Skin-Tension Feeling>
◯: At least 7 out of 10 panelists answered "have a skin-tension feeling".
Δ: Four to 6 out of 10 panelists answered "have a skin-tension feeling".
x: Not more than 3 out of 10 panelists answered "have a skin-tension feeling".

<Evaluation of Adhesiveness to the Skin>
◯: At least 7 out of 10 panelists answered "have a skin-adhesiveness feeling".
Δ: Four to 6 out of 10 panelists answered "have a skin-adhesiveness feeling".
x: Not more than 3 out of 10 panelists answered "have a skin-adhesiveness feeling".

<Evaluation of Non-Sticky Feeling>
◯: At least 7 out of 10 panelists answered "non-sticky feeling".
Δ: Four to 6 out of 10 panelists answered "non-sticky feeling".
x: Not more than 3 out of 10 panelists answered "non-sticky feeling".

TABLE 10

|  | Example | | | Comparative Example | |
|---|---|---|---|---|---|
|  | 10 | 11 | 12 | 3 | 4 |
| Carnauba wax | — | 0.5 | — | — | 0.5 |
| Candelilla wax | 1 | — | 0.2 | — | — |
| POE(20)behenyl ether | 1.5 | 2 | 5 | 0.5 | 0.5 |
| Carboxyvinyl polymer | 0.4 | 0.4 | 0.3 | 0.2 | 0.4 |
| Potassium hydroxide | 0.1 | 0.1 | 0.08 | 0.05 | 0.11 |
| Dimethyl polysiloxane | 2 | 1 | 0.1 | 0.1 | — |
| Ion-exchange water | bal. | bal. | bal. | bal. | bal. |
| skin-tension feeling | ◯ | ◯ | Δ | x | ◯ |
| adhesiveness to the skin | ◯ | ◯ | Δ | x | ◯ |
| non-sticky feeling | ◯ | ◯ | ◯ | ◯ | x |
| Average particle size of wax (nm) | 36 | 34 | 35 | — | 32 |

Set forth below are formulae that can be applied in the present invention.

[Compounding formula 5: Beauty lotion]

| (Ingredients to be compounded) | (mass %) |
|---|---|
| (1) Carnauba wax | 1.5 |
| (2) POE(20)behenyl ether | 1.8 |
| (3) Carboxyvinyl polymer | 0.3 |
| (4) Potassium hydroxide | 0.1 |
| (5) Tocopherol acetate | 0.05 |
| (6) Glycerin | 5 |
| (7) Dimethyl polysiloxane | 2 |
| (8) Ion-exchange water | bal. |
| (9) Perfume | q.s. |
| (10) Phenoxyethanol | 0.5 |

(Method of Production)

Ingredients (1), (2), (5) and (9), as well as portions of ingredients (6) and (8) were mixed under stirring at about 95° C. until the mixture became clear; thereafter, it was ice-cooled to make a fine dispersion of the wax; the fine dispersion of the wax was added to a mixture of the remaining portions of (6) and (8) with a mixture of ingredients (3), (4) and (10) to make a beauty lotion.

[Compounding formula 6: Skin-lightening jelly]

| (Ingredients to be compounded) | (mass %) |
|---|---|
| (1) Carnauba wax | 0.5 |
| (2) Candelilla wax | 0.3 |
| (3) Rice wax | 0.2 |
| (4) Beeswax | 0.1 |
| (5) Microcrystalline wax | 0.1 |
| (6) Paraffin wax | 0.1 |
| (7) Petrolatum | 0.1 |
| (8) Behenyl alcohol | 0.1 |
| (9) Stearyl alcohol | 0.03 |
| (10) POE(10)behenyl ether | 0.1 |
| (11) POE(20)behenyl ether | 1.5 |
| (12) POE(30)behenyl ether | 0.1 |
| (13) POE(20)glyceryl ether isostearic acid ester | 0.1 |
| (14) Retinol palmitate | 0.01 |
| (15) α-Tocopherol | 0.01 |
| (16) Tetraisopalmitoylascorbyl | 0.01 |
| (17) Isobutyl resorcine | 0.01 |
| (18) Linoleic acid | 0.03 |
| (19) Linolenic acid | 0.02 |
| (20) Ascorbic acid phosphate sodium salt | 0.01 |
| (21) Ascorbic acid phosphate magnesium salt | 0.01 |
| (22) Ascorbic acid 2-glucoside | 2 |
| (23) Ethyl ascorbate | 0.01 |

[Compounding formula 6: Skin-lightening jelly]

| (Ingredients to be compounded) | (mass %) |
|---|---|
| (24) Pantothenylethyl ether | 0.01 |
| (25) Arbutin | 0.01 |
| (26) Methyl tranexamate amide salt | 1 |
| (27) Dipotassium glycyrrhizinate | 0.01 |
| (28) 4-Methoxysalicylic acid salt | 1 |
| (29) Glycerin | 1 |
| (30) Dipropylene glycol | 10 |
| (31) Polyoxyethylene glycol | 1 |
| (32) Paraoxybenzoic acid ester | 0.15 |
| (33) Phenoxyethanol | 0.3 |
| (34) Trisodium edetate | 0.02 |
| (35) Citric acid | q.s. |
| (36) Sodium citrate | q.s. |
| (37) Potassium hydroxide | q.s. |
| (38) Methyl polysiloxane | 2 |
| (39) Phenyl polysiloxane | 1 |
| (40) Carboxyvinyl polymer | 0.2 |
| (41) Acrylic acid/alkyl($C_{10-30}$) acrylate copolymer | 0.51 |
| (42) 2-Methacryloyloxyethylphosphorylcholine/butyl methacrylate copolymer | 0.1 |
| (43) Ethanol | 10 |
| (44) Perfume | q.s. |
| (45) Ion-exchange water | bal. |

[Compounding formula 7: Skin roughness ameliorating cream]

| (Ingredients to be compounded) | (mass %) |
|---|---|
| (1) Carnauba wax | 0.8 |
| (2) Candelilla wax | 0.2 |
| (3) Beeswax | 0.1 |
| (4) Microcrystalline wax | 0.1 |
| (5) Petrolatum | 0.1 |
| (6) Liquid paraffin | 0.1 |
| (7) Squalane | 0.1 |
| (8) POE(20)behenyl ether | 2 |
| (9) POP(1)POE(15)behenyl ether | 0.2 |
| (10) POE(20)glyceryl ether isostearic acid ester | 0.8 |
| (11) α-Tocopherol | 0.01 |
| (12) Tocopherol acetate | 0.01 |
| (13) Stearyl glycyrrhetinate | 0.01 |
| (14) Oil-soluble vitamin B | 0.01 |
| (15) Dibutylhydroxytoluene | 0.01 |
| (16) Benzyl nicotinate | 0.01 |
| (17) Tranexamic acid | 0.5 |
| (18) Methyl tranexamate amide salt | 0.1 |
| (19) 4-Methoxysalicylic acid salt | 0.5 |
| (20) Nicotinic acid | 0.01 |
| (21) Nicotinic acid amide | 0.01 |
| (22) Hydroxyproline | 0.01 |
| (23) Serine | 0.01 |
| (24) Thiotaurine | 0.01 |
| (25) Arginine | 0.01 |
| (26) Trimethylglycine | 0.01 |
| (27) Erythritol | 5 |
| (28) Glycerin | 2 |
| (29) Butylene glycol | 5 |
| (30) Dipropylene glycol | 5 |
| (31) Polyoxyethylene glycol | 2 |
| (32) Phenoxyethanol | 0.5 |
| (33) Trisodium edetate | 0.02 |
| (34) Citric acid | q.s. |
| (35) Sodium citrate | q.s. |
| (36) Potassium hydroxide | q.s. |
| (37) Methyl polysiloxane | 2 |
| (38) Phenyl polysiloxane | 1 |
| (39) Decamethylcyclopentasiloxane | 5 |
| (40) Cetyl 2-ethylhexanoate | 1 |
| (41) Bleached beeswax | 1 |
| (42) Batyl alcohol | 1.65 |
| (43) Behenyl alcohol | 0.77 |
| (44) Acrylic acid/alkyl ($C_{10-30}$) acrylate copolymer | 0.3 |

[Compounding formula 7: Skin roughness ameliorating cream]

| (Ingredients to be compounded) | (mass %) |
|---|---|
| (45) Ethanol | 5 |
| (46) Perfume | q.s. |
| (47) Ion-exchange water | bal. |

[Compounding formula 8: Moisturizing jelly]

| (Ingredients to be compounded) | (mass %) |
|---|---|
| (1) Carnauba wax | 0.5 |
| (2) Rice wax | 0.4 |
| (3) Paraffin wax | 0.1 |
| (4) POE cholesterol ether | 0.1 |
| (5) Glyceryl stearate | 0.05 |
| (6) Hydrogenated castor oil | 0.1 |
| (7) Behenyl alcohol | 0.2 |
| (8) Batyl alcohol | 0.05 |
| (9) Stearic acid | 0.05 |
| (10) Triglycerin | 0.05 |
| (11) Glycerol Trioctanoate | 0.05 |
| (12) Paraffin | 0.1 |
| (13) POE(10)behenyl ether | 0.7 |
| (14) POE(30)behenyl ether | 0.8 |
| (15) POP(1)POE(15)behenyl ether | 0.2 |
| (16) POE(20)glyceryl ether isostearic acid ester | 0.01 |
| (17) POE(60) hydrogenated castor oil | 0.5 |
| (18) Tocopherol acetate | 0.01 |
| (19) Stearyl glycyrrhetinate | 0.01 |
| (20) Ubiquinone | 0.01 |
| (21) β-Carotene | 0.01 |
| (22) Vitamin $D_2$ (= ergocalciferol) | 0.005 |
| (23) γ-Orizanol | 0.01 |
| (24) Ascorbic acid phosphate magnesium salt | 1 |
| (25) Nicotinic acid | 0.01 |
| (26) Urea | 2 |
| (27) Hyaluronic acid | 0.001 |
| (28) Acetylated hyaluronic acid | 0.001 |
| (29) Trehalose | 1 |
| (30) Erythritol | 1 |
| (31) Xylitol | 1 |
| (32) Glycerin | 5 |
| (33) Polyoxyethylene glycol | 5 |
| (34) POE-POP dimethyl ether | 1 |
| (35) Phenoxyethanol | 0.5 |
| (36) Trisodium edetate | 0.02 |
| (37) Citric acid | q.s. |
| (38) Sodium citrate | q.s. |
| (39) Potassium hydroxide | q.s. |
| (40) methyl polysiloxane | 1 |
| (41) phenyl polysiloxane | 1 |
| (42) Behenyl alcohol | 0.1 |
| (43) Agar | 2.5 |
| (44) Dimethyl acrylamide/sodium acryloyldimethyl taurate crosspolymer | 0.1 |
| (45) Perfume | q.s. |
| (46) Ion-exchange water | bal. |

[Compounding formula 9: UV preventing jelly]

| (Ingredients to be compounded) | (mass %) |
|---|---|
| (1) Carnauba wax | 0.4 |
| (2) Beeswax | 0.5 |
| (3) Paraffin wax | 0.1 |
| (4) POE cholesterol ether | 0.1 |
| (5) Hydrogenated castor oil | 0.1 |
| (6) Behenyl alcohol | 0.5 |
| (7) Batyl alcohol | 0.1 |
| (8) Stearic acid | 0.05 |
| (9) Triglycerin | 0.05 |

-continued

[Compounding formula 9: UV preventing jelly]

| (Ingredients to be compounded) | (mass %) |
|---|---|
| (10) Pentaerythritol tetraoctanoate | 0.1 |
| (11) POE(20)behenyl ether | 1.8 |
| (12) POE(20)glyceryl ether isostearic acid ester | 1.5 |
| (13) POE(60)glyceryl ether isostearic acid ester | 0.03 |
| (14) Tocopherol acetate | 0.01 |
| (15) Stearyl glycyrrhetinate | 0.01 |
| (16) Isobutyl resorcine | 0.01 |
| (17) Octocrylene | 0.05 |
| (18) Octyl methoxycinnamate | 0.05 |
| (19) Tranexamic acid | 1 |
| (20) Methyl tranexamate amide salt | 1 |
| (21) Nicotinic acid amide | 0.01 |
| (22) Hydroxyproline | 0.01 |
| (23) Glycerin | 10 |
| (24) Butylene glycol | 5 |
| (25) Polyoxyethylene glycol | 1 |
| (26) POE-POP dimethyl ether | 5 |
| (27) Paraoxybenzoic acid ester | 0.1 |
| (28) Phenoxyethanol | 0.5 |
| (29) Trisodium edentate | 0.02 |
| (30) Citric acid | q.s. |
| (31) Sodium citrate | q.s. |
| (32) Potassium hydroxide | q.s. |
| (33) Perfluoropolyether | 3 |
| (34) Phenyl polysiloxane | 2 |
| (35) Carboxyvinyl polymer | 0.5 |
| (36) Acrylic acid/alkyl($C_{10-30}$) acrylate copolymer | 0.5 |
| (37) Ethanol | 5 |
| (38) Perfume | q.s. |
| (39) Ion-exchange water | bal. |

INDUSTRIAL APPLICABILITY

It is provided by the present invention skin external preparations which are stable and are superior in a skin-tension feeling effect after application therewith to the skin. It is also provided by the present invention skin external preparations which are excellent in adhesiveness to the skin and have a non-sticky feeling, in addition to the stability and the skin-tension feeling effect.

The invention claimed is:

1. A skin external preparation comprising a finely dispersed wax composition, wherein the wax is finely dispersed in a solid or semisolid form in an aqueous dispersion medium the wax is solid or semisolid at room temperature, and is present in an amount of 0.01 to 25 mass % in the total amount of the finely dispersed wax composition, and further comprising a nonionic surfactant which contains one or more selected from among polyoxyethylene alkyl ethers, polyoxyethylene-polyoxypropylene alkyl ethers, polyoxyethylene glyceryl ether fatty acid esters, polyoxyethylene castor oil, and polyoxyethylene hydrogenated castor oil and their derivatives, an ionic water-soluble thickener, and at least one of silicone oil and fluorinated oil which is liquid at room temperature in an amount of 0.1 to 10 mass % in the total amount of the finely dispersed wax composition, the mass ratio of the nonionic surfactant to the wax being 1.1 or more, the particle size of the finely dispersed wax is 500 nm or less, the HLB of the nonionic surfactant or weight-average HLB for all nonionic surfactants in the finely dispersed wax composition is in the range of 11-14, and the preparation contains substantially no ionic surfactants therein.

2. The skin external preparation according to claim 1, wherein (a) at least one of polyoxyethylene alkyl ethers and polyoxyethylene-polyoxypropylene alkyl ethers, and (b) polyoxyethylene glyceryl ether fatty acid esters are contained as nonionic surfactants.

3. The skin external preparation according to claim 1, wherein the polyoxyethylene alkyl ethers and polyoxyethylene-polyoxypropylene alkyl ethers are one or more selected from among compounds represented by at least one of the following formulas (I) and (II):

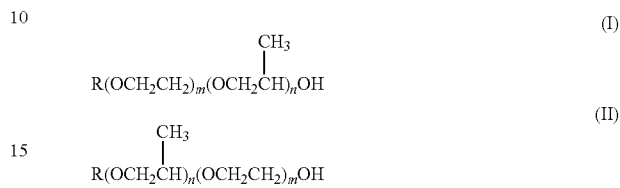

wherein in the formulas (I) and (II), R represents an alkyl or alkenyl group having 12-24 carbon atoms, m represents a number of 5-30, and n represents a number of 0-5.

4. The skin external preparation according to claim 1, wherein the ionic water-soluble thickener is one or more selected from among alginate polymers, vinyl polymers, acryl polymers, polyethyleneimide, and cationized polymers.

5. The skin external preparation according to claim 1, wherein the finely dispersed wax composition is obtained by a process wherein
 (a) the wax,
 (b) the nonionic surfactant, and
 (c) the aqueous dispersion medium, with the mass ratio of the nonionic surfactant to the wax being 1.1 or more, the HLB of the nonionic surfactant or weight-average HLB for all nonionic surfactants in the finely dispersed wax composition is in the range of 11-14 is heated to a temperature not lower than the melting point of the wax but within the solubilizing temperature range so that the wax becomes solubilized and the system is thereafter cooled to room temperatures, and then added thereinto the ionic water-soluble thickener and at least one of silicone oil and fluorinated oil which is liquid at room temperature.

6. The skin external preparation according to claim 1, wherein the nonionic surfactant consists of one or more selected from a group consisting of polyoxyethylene alkyl ethers, polyoxyethylene-polyoxypropylene alkyl ethers, polyoxyethylene glyceryl ether fatty acid esters, polyoxyethylene castor oil and their derivatives.

7. The skin external preparation according to claim 1, wherein the wax has a melting point of 80° C. or more.

8. The skin external preparation according to claim 1, wherein the wax consists of one or more selected from a group consisting of beeswax, candelilla wax, cotton wax, carnauba wax, bayberry wax, insect wax, spermaceti, montan wax, bran wax, capok wax, Japan wax, lanolin acetate, sugar cane wax, esters of lanolin fatty acids and isopropyl alcohol, hexyl laurate, reduced lanolin, jojoba wax, hard lanolin, shellac wax, microcrystalline wax, paraffin wax, POE lanolin alcohol ethers, POE lanolin alcohol acetates, POE cholesterol ethers, esters of lanolin fatty acids and polyethylene glycol, fatty acid glycerides, hydrogenated castor oil, petrolatum, and POE hydrogenated lanolin alcohol ethers.

9. The skin external preparation according to claim 1, wherein the ionic water-soluble thickener is contained in the finely dispersed wax composition in an amount of 0.01 to 5 mass % in the total amount of the finely dispersed wax composition.

10. The skin external preparation according to claim 1, wherein the ionic water-soluble thickener is contained in the finely dispersed wax composition in an amount of 0.1 to 2 mass % in the total amount of the finely dispersed wax composition.

\* \* \* \* \*